United States Patent
Stoltz et al.

(10) Patent No.: US 7,361,171 B2
(45) Date of Patent: *Apr. 22, 2008

(54) MAN-PORTABLE OPTICAL ABLATION SYSTEM

(75) Inventors: Richard Stoltz, Plano, TX (US); Jeff Bullington, Chuluota, FL (US)

(73) Assignee: Raydiance, Inc., Orlando, FL (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/916,017

(22) Filed: Aug. 11, 2004

(65) Prior Publication Data

US 2005/0171516 A1  Aug. 4, 2005

Related U.S. Application Data

(63) Continuation-in-part of application No. PCT/US2004/015913, filed on May 19, 2004.

(60) Provisional application No. 60/503,578, filed on Sep. 17, 2003, provisional application No. 60/494,321, filed on Aug. 11, 2003, provisional application No. 60/471,971, filed on May 20, 2003.

(51) Int. Cl.
*A61B 18/18* (2006.01)

(52) U.S. Cl. .............. 606/9; 606/10; 607/88; 128/898

(58) Field of Classification Search .......... 606/3–12, 606/88, 89; 128/898; 216/65, 66, 87; 359/333, 359/342–3

See application file for complete search history.

(56) References Cited

U.S. PATENT DOCUMENTS

| | | | |
|---|---|---|---|
| 3,631,362 A | 12/1971 | Almasi et al. | |
| 3,808,549 A | 4/1974 | Maurer | |
| 3,963,953 A | 6/1976 | Thornton, Jr. | |
| 4,718,418 A | 1/1988 | L'Esperance, Jr. | |
| 4,750,809 A | 6/1988 | Kafka et al. | |
| 4,815,079 A | 3/1989 | Snitzer et al. | |
| 4,824,598 A | 4/1989 | Stokowski | |
| 4,829,529 A | 5/1989 | Kafka | |
| 4,902,127 A | 2/1990 | Byer et al. | |
| 4,913,520 A | 4/1990 | Kafka | |
| 4,972,423 A | 11/1990 | Alfano et al. | |

(Continued)

FOREIGN PATENT DOCUMENTS

JP  2003181661 A  7/2003

(Continued)

OTHER PUBLICATIONS

U.S. Appl. No. 10/916,368, Richard Stoltz, Pulse Energy Adjustment for Changes in Ablation Spot Size, filed Aug. 11, 2004.

(Continued)

*Primary Examiner*—A. Farah
(74) *Attorney, Agent, or Firm*—Carr & Ferrell LLP

(57) ABSTRACT

The present invention includes an apparatus and method of surgical ablative material removal "in-vivo" or from an outside surface with a short optical pulse that is amplified and compressed using either an optically-pumped-amplifier and air-path between gratings compressor combination or a SOA and chirped fiber compressor combination, wherein the generating, amplifying and compressing are done within a man-portable system.

24 Claims, 2 Drawing Sheets

U.S. PATENT DOCUMENTS

| | | |
|---|---|---|
| 5,098,426 A | 3/1992 | Sklar et al. |
| 5,162,643 A | 11/1992 | Currie |
| 5,166,818 A | 11/1992 | Chase et al. |
| 5,187,759 A | 2/1993 | DiGiovanni et al. |
| 5,237,576 A | 8/1993 | DiGiovanni et al. |
| 5,265,107 A | 11/1993 | Delfyett, Jr. |
| 5,291,501 A | 3/1994 | Hanna |
| 5,302,835 A | 4/1994 | Bendett et al. |
| 5,313,262 A | 5/1994 | Leonard |
| 5,329,398 A | 7/1994 | Lai et al. |
| 5,400,350 A | 3/1995 | Galvanauskas |
| 5,414,725 A | 5/1995 | Fermann et al. |
| 5,418,809 A | 5/1995 | August, Jr. et al. |
| 5,430,572 A | 7/1995 | DiGiovanni et al. |
| 5,440,573 A | 8/1995 | Fermann |
| 5,450,427 A | 9/1995 | Fermann et al. |
| 5,479,422 A | 12/1995 | Fermann et al. |
| 5,489,984 A | 2/1996 | Hariharan et al. |
| 5,499,134 A | 3/1996 | Galvanauskas et al. |
| 5,517,043 A | 5/1996 | Ma et al. |
| 5,572,335 A | 11/1996 | Stevens |
| 5,572,358 A | 11/1996 | Gabl et al. |
| 5,585,652 A | 12/1996 | Kamasz et al. |
| 5,585,913 A | 12/1996 | Hariharan et al. |
| 5,592,327 A | 1/1997 | Gabl et al. |
| 5,596,668 A | 1/1997 | DiGiovanni et al. |
| 5,602,677 A | 2/1997 | Tournois |
| 5,617,434 A | 4/1997 | Tamura et al. |
| 5,627,848 A | 5/1997 | Fermann et al. |
| 5,633,750 A | 5/1997 | Nogiwa et al. |
| 5,633,885 A | 5/1997 | Galvanauskas et al. |
| 5,656,186 A | 8/1997 | Mourou et al. |
| 5,663,731 A | 9/1997 | Theodoras, II et al. |
| 5,677,769 A | 10/1997 | Bendett |
| 5,689,519 A | 11/1997 | Fermann et al. |
| 5,696,782 A | 12/1997 | Harter et al. |
| 5,701,319 A | 12/1997 | Fermann |
| 5,703,639 A | 12/1997 | Farrier et al. |
| 5,708,669 A | 1/1998 | DiGiovanni et al. |
| 5,710,424 A | 1/1998 | Theodoras, II et al. |
| 5,720,894 A | 2/1998 | Neev et al. |
| 5,726,855 A | 3/1998 | Mourou et al. |
| 5,778,016 A | 7/1998 | Sucha et al. |
| 5,788,688 A | 8/1998 | Bauer et al. |
| 5,818,630 A | 10/1998 | Fermann et al. |
| 5,822,097 A | 10/1998 | Tournois |
| 5,847,863 A | 12/1998 | Galvanauskas et al. |
| 5,862,287 A | 1/1999 | Stock et al. |
| 5,867,304 A | 2/1999 | Galvanauskas et al. |
| 5,875,408 A | 2/1999 | Bendett et al. |
| 5,880,823 A | 3/1999 | Lu |
| 5,880,877 A | 3/1999 | Fermann et al. |
| 5,898,485 A | 4/1999 | Nati, Jr. |
| 5,920,668 A | 7/1999 | Uehara et al. |
| 5,923,686 A | 7/1999 | Fermann et al. |
| 5,936,716 A | 8/1999 | Pinsukanjana et al. |
| 6,014,249 A | 1/2000 | Fermann et al. |
| 6,020,591 A | 2/2000 | Harter et al. |
| 6,034,975 A | 3/2000 | Harter et al. |
| 6,061,373 A | 5/2000 | Brockman et al. |
| 6,072,811 A | 6/2000 | Fermann et al. |
| 6,075,588 A | 6/2000 | Pinsukanjana et al. |
| 6,081,369 A | 6/2000 | Waarts et al. |
| 6,120,857 A | 9/2000 | Balooch et al. |
| 6,130,780 A | 10/2000 | Joannopoulos et al. |
| 6,151,338 A | 11/2000 | Grubb et al. |
| 6,154,310 A | 11/2000 | Galvanauskas et al. |
| 6,156,030 A * | 12/2000 | Neev ................ 606/10 |
| 6,181,463 B1 | 1/2001 | Galvanauskas et al. |
| 6,198,568 B1 | 3/2001 | Galvanauskas et al. |
| 6,208,458 B1 | 3/2001 | Galvanauskas et al. |
| 6,249,630 B1 | 6/2001 | Stock et al. |
| 6,252,892 B1 | 6/2001 | Jiang et al. |
| 6,256,328 B1 | 7/2001 | Delfyett et al. |
| 6,269,108 B1 | 7/2001 | Tabirian et al. |
| 6,275,512 B1 | 8/2001 | Fermann |
| 6,303,903 B1 | 10/2001 | Liu |
| 6,314,115 B1 | 11/2001 | Delfyett et al. |
| 6,327,074 B1 | 12/2001 | Bass et al. |
| 6,327,282 B2 | 12/2001 | Hammons et al. |
| 6,334,011 B1 | 12/2001 | Galvanauskas et al. |
| 6,335,821 B1 | 1/2002 | Suzuki et al. |
| RE37,585 E | 3/2002 | Mourou et al. |
| 6,355,908 B1 | 3/2002 | Tatah et al. |
| 6,362,454 B1 | 3/2002 | Liu |
| 6,365,869 B1 | 4/2002 | Swain et al. |
| 6,404,944 B1 | 6/2002 | Wa et al. |
| 6,421,169 B1 | 7/2002 | Bonnedal et al. |
| 6,433,303 B1 | 8/2002 | Liu et al. |
| 6,433,305 B1 | 8/2002 | Liu et al. |
| 6,433,760 B1 | 8/2002 | Vaissie et al. |
| 6,501,590 B2 | 12/2002 | Bass et al. |
| 6,522,460 B2 | 2/2003 | Bonnedal et al. |
| 6,525,873 B2 | 2/2003 | Gerrish et al. |
| 6,526,327 B2 | 2/2003 | Kar et al. |
| 6,529,319 B2 | 3/2003 | Youn et al. |
| 6,549,547 B2 | 4/2003 | Galvanauskas et al. |
| 6,567,431 B2 | 5/2003 | Tabirian et al. |
| 6,573,813 B1 | 6/2003 | Joannopoulos et al. |
| 6,574,024 B1 | 6/2003 | Liu |
| 6,576,917 B1 | 6/2003 | Silfvast |
| 6,580,553 B2 | 6/2003 | Kim et al. |
| 6,597,497 B2 | 7/2003 | Wang et al. |
| 6,603,911 B2 | 8/2003 | Fink et al. |
| 6,621,045 B1 | 9/2003 | Liu et al. |
| 6,627,844 B2 | 9/2003 | Liu et al. |
| 6,642,477 B1 | 11/2003 | Patel et al. |
| 6,647,031 B2 | 11/2003 | Delfyett et al. |
| 6,654,161 B2 | 11/2003 | Bass et al. |
| 6,661,816 B2 | 12/2003 | Delfyett et al. |
| 6,671,298 B1 | 12/2003 | Delfyett et al. |
| 6,690,686 B2 | 2/2004 | Delfyett et al. |
| 6,695,835 B2 | 2/2004 | Furuno et al. |
| 6,710,288 B2 | 3/2004 | Liu et al. |
| 6,710,293 B2 | 3/2004 | Liu et al. |
| 6,711,334 B2 | 3/2004 | Szkopek et al. |
| 6,720,519 B2 | 4/2004 | Liu et al. |
| 6,723,991 B1 | 4/2004 | Sucha et al. |
| 6,728,439 B2 | 4/2004 | Weisberg et al. |
| 6,735,229 B1 | 5/2004 | Delfyett et al. |
| 6,738,144 B1 | 5/2004 | Dogariu |
| 6,744,555 B2 | 6/2004 | Galvanauskas et al. |
| 6,749,285 B2 | 6/2004 | Liu et al. |
| 6,760,356 B2 | 7/2004 | Erbert et al. |
| 6,774,869 B2 | 8/2004 | Biocca et al. |
| 6,782,207 B1 | 8/2004 | Efimov |
| 6,787,734 B2 | 9/2004 | Liu |
| 6,788,864 B2 | 9/2004 | Ahmad et al. |
| 6,791,060 B2 | 9/2004 | Dunsky et al. |
| 6,801,551 B1 | 10/2004 | Delfyett et al. |
| 6,803,539 B2 | 10/2004 | Liu et al. |
| 6,804,574 B2 | 10/2004 | Liu et al. |
| 6,807,375 B2 | 10/2004 | Dogariu |
| 6,815,638 B2 | 11/2004 | Liu |
| 6,819,694 B2 | 11/2004 | Jiang et al. |
| 6,819,837 B2 | 11/2004 | Li et al. |
| 6,822,251 B1 | 11/2004 | Arenberg et al. |
| 6,829,517 B2 | 12/2004 | Cheng et al. |
| 6,878,900 B2 | 4/2005 | Corkum et al. |
| 6,897,405 B2 | 5/2005 | Cheng et al. |
| 6,928,490 B1 | 8/2005 | Bucholz et al. |
| 7,022,119 B2 | 4/2006 | Hohla |
| 7,143,769 B2 * | 12/2006 | Stoltz et al. ............. 128/898 |
| 7,217,266 B2 | 5/2007 | Anderson et al. |

| 2002/0176676 | A1 | 11/2002 | Johnson et al. |
| 2003/0060808 | A1 | 3/2003 | Wilk |
| 2003/0161378 | A1 | 8/2003 | Zhang et al. |
| 2004/0231682 | A1 | 11/2004 | Stoltz |
| 2005/0035097 | A1 | 2/2005 | Stoltz |
| 2005/0061779 | A1 | 3/2005 | Blumenfeld et al. |
| 2005/0065502 | A1 | 3/2005 | Stoltz |
| 2005/0074974 | A1 | 4/2005 | Stoltz |
| 2005/0077275 | A1 | 4/2005 | Stoltz |
| 2005/0127049 | A1 | 6/2005 | Woeste et al. |
| 2005/0167405 | A1 | 8/2005 | Stoltz et al. |
| 2005/0171518 | A1 | 8/2005 | Stoltz et al. |
| 2005/0175280 | A1 | 8/2005 | Nicholson |
| 2005/0177143 | A1 | 8/2005 | Bullington et al. |
| 2005/0195726 | A1 | 9/2005 | Bullington et al. |
| 2006/0067604 | A1 | 3/2006 | Bull et al. |
| 2006/0120418 | A1 | 6/2006 | Harter et al. |

FOREIGN PATENT DOCUMENTS

| WO | WO 2004/105100 A2 | 12/2004 |
| WO | WO 2004/114473 A2 | 12/2004 |
| WO | WO 2005/018060 A2 | 2/2005 |
| WO | WO 2005/018061 A2 | 2/2005 |
| WO | WO 2005/018062 A2 | 2/2005 |
| WO | WO 2005/018063 A2 | 2/2005 |

OTHER PUBLICATIONS

U.S. Appl. No. 10/850,325, Richard Stoltz, Controlling Temperature of an Optical Amplifier by Controlling Pump Diode Current, filed May 19, 2004.

U.S. Appl. No. 11/057,867, Michael Marshall Mielke, Method of Generating an Ultra-Short Pulse Using a High-Frequency Ring Oscillator, filed Feb. 13, 2005.

U.S. Appl. No. 11/057,868, Michael Marshall Mielke, Amplifying of high Energy Laser Pulses, filed Feb. 13, 2005.

U.S. Appl. No. 11/224,867, Peter Delfyett, Laser Ablation Method and Apparatus Having a Feedback Loop and Control Unit, filed Sep. 12, 2005.

U.S. Appl. No. 11/233,634, James F. Brennan, III, Wavelength-Stabilized Pump Diodes for Pumping Gain Media in an Ultrashort Pulsed Laser System, filed Sep. 22, 2005.

U.S. Appl. No. 11/112,256, James F. Brennan, III, Bragg Fibers in Systems for the Generation of High Peak Power Light, filed Apr. 22, 2005.

U.S. Appl. No. 11/229,302, Michael Marshall Mielke, Actively Stabilized Systems for the Generation of Ultrashort Optical Pulses, filed Sep. 15, 2005.

U.S. Appl. No. 10/916,365, Richard Stoltz, Ablative Material Removal with a Preset Removal Rate or Volume or Depth, filed Aug. 11, 2005.

Yeh et al., "Theory of Bragg Fiber", Journal of the Optical Society America, Sep. 1978, pp. 1196, vol. 68, No. 9.

Engeness et al., "Dispersion Talloring and Compensation by Modal Interations in Omniguide Fibers," Optics Express, May 19, 2003, pp. 1175-1196, vol. 11, No. 10.

Fink et al., "Guiding Optical Light in Air Using an All-Dielectric Structure," Journal of Lightwave Technology, Nov. 1999, pp. 2039-2041, vol. 17, No. 11.

Siegman, "Unstable Optical Resonators", Applied Optics, Feb. 1974, pp. 353-367, vol. 13, No. 2.

Koechner, "Solid State Laser Engineering", Oct. 29, 1999, Section 5.5, pp. 270-277, 5th Edition, Springer.

Chen et al. "Dispersion-Managed Mode Locking", Journal of the Optical Society of America B, Nov. 1999, pp. 1999-2004, vol. 16, No. 11, Optical Society of America.

Resan et al. "Dispersion-Managed Semiconductor Mode-Locked Ring Laser", Optics Letters, Aug. 1, 2003, pp. 1371-1373, vol. 28, No. 15, Optical Society of America.

Dasgupta, S. et al., "Design of Dispersion-Compensating Bragg Fiber with an Ultrahigh Figure of Merit," Optics Letters Aug. 1, 2005, pp. 1917-1919, vol. 30, No. 15, Optical Society of America.

Mohammed, W. et al., "Selective Excitation of the TE01 Mode in Hollow-Glass Waveguide Using a Subwavelength Grating," IEEE Photonics Technology Letters, Jul. 2005, vol. 17, No. 7, IEEE.

Delfyett, P et al., "Ultrafast Semiconductor Laser-Diode-Seeded Cr:LiSAF Rengerative Amplifier System", Applied Optics, May 20, 1997, pp. 3375-3380, vol. 36, No. 15, Octoical Society of America.

Levy et al., "Engineering Space-Variant INhomogeneous Media for Polarization Control," Optics Letters, Aug. 1, 2004, pp. 1718-1720, vol. 29, No. 15, Optical Society of America.

Ibanescu et al., "Analysis of Mode Structure in Hollow Dielectric Waveguide Fibers," Physical Review E 67, 2003, The American Physical Society.

Limpert et al., "All Fiber Chirped-Pulse Amplification System Based on Compression in Air-Guiding Photonic Bandgap Fiber", Optics Express, Dec. 1, 2003, vol. 11, No. 24, pp. 3332-3337.

Price et al., "Advances in High Power, Short Pulse, Fiber Laser Systems and Technology", Proceedings of SPIE—vol. 5709, Fiber Lasers II: Technology, Systems, and Applications, Apr. 2005, pp. 184-192.

* cited by examiner

MAN-PORTABLE OPTICAL ABLATION SYSTEM

CROSS-REFERENCE TO RELATED APPLICATIONS

This application is a continuation-in-part of patent application Ser. No. PCT/US2004/015913 filed May 19, 2004 and titled "Trains of Ablation Pulses from Multiple Optical Amplifiers" which claims the benefit of U.S. Provisional Patent Application Ser. No. 60/471,971 filed on May 20, 2003 and titled "Stretched Optical Pulse Amplification and Compression," U.S. Provisional Patent Application Ser. No. 60/471,922 filed on May 20, 2003 and titled "Laser Machining," and U.S. Provisional Patent Application Ser. No. 60/503,578 filed on Sep. 17, 2003 and titled "Controlling Optically-Pumped Optical Pulse Amplifiers;" this application also claims the benefit of U.S. Provisional Patent Application Ser. No. 60/494,321 filed on Aug. 11, 2003 and titled "Man-Portable Optical Ablation System."

TECHNICAL FIELD OF THE INVENTION

The present invention relates in general to the field of light amplification and more particularly to altering the emission of an ablation beam for safety or control.

BACKGROUND OF THE INVENTION

Ablative material removal is especially useful for medical purposes, either in-vivo or on the outside surface (e.g., skin or tooth), as it is essentially non-thermal and generally painless. Ablative removal of material is generally done with a short optical pulse that is stretched, amplified and then compressed. A number of types of laser amplifiers have been used for the amplification, including fiber-amplifiers. Fiber amplifiers have a storage lifetime of about 100 to 300 microseconds. While some measurements have been made at higher repetition rates, these measurements have shown an approximately linear decrease in pulse energy, and for ablations purposes, fiber amplifiers have been operated with a time between pulses of equal to or greater than the storage lifetime, and, thus, are generally run a rep rate of less than 3-10 kHz.

Laser machining can remove ablatively material by dis-associate the surface atoms and melting the material. Laser ablation is done efficiently with a beam of short pulses (generally a pulse-duration of three picoseconds or less). Techniques for generating these ultra-short pulses (USP) are described, e.g., in a book entitled "Femtosecond Laser Pulses" (C. Rulliere, editor), published 1998, Springer-Verlag Berlin Heidelberg New York. Generally large systems, such as Ti:Sapphire, are used for generating ultra-short pulses (USP).

USP phenomenon was first observed in the 1970's, when it was discovered that mode-locking a broad-spectrum laser could produce ultra-short pulses. The minimum pulse duration attainable is limited by the bandwidth of the gain medium, which is inversely proportional to this minimal or Fourier-transform-limited pulse duration. Mode-locked pulses are typically very short and will spread (i.e., undergo temporal dispersion) as they traverse any medium. Subsequent pulse-compression techniques are often used to obtain USP's. Pulse dispersion can occur within the laser cavity so that compression techniques are sometimes added intra-cavity. When high-power pulses are desired, they are intentionally lengthened before amplification to avoid internal component optical damage. This is referred to as "Chirped Pulse Amplification" (CPA). The pulse is subsequently compressed to obtain a high peak power (pulse-energy amplification and pulse-duration compression).

SUMMARY OF THE INVENTION

Ablative material removal with a short optical pulse is especially useful for medical purposes and can be done either in-vivo or on the body surface, as it is essentially non-thermal and generally painless. Previously, ablative systems include optical benches weighing perhaps 1,000 pounds and occupying about 300 cubic feet. One embodiment of the present invention includes a system that weighs 100 pounds or less and occupies 2.5 cubic feet or less.

One embodiment of the present invention includes an amplifier and a pulse-compressor, enabling the invention to be man-portable. As used herein, the term "man-portable" generally means capable of being moved reasonably easily by one person. In one embodiment, the man-portable system is a wheeled cart. In another embodiment, the man-portable system is a backpack.

One embodiment of the man-portable unit includes a handheld probe, vest/backpack and two or more satchels. Other embodiments include handheld probe, vest and backpack. The unit can be relatively inexpensive and can be used by surgeons, doctors, dentists, scientists and emergency personnel in the field. However, those skilled in the art will recognize other uses for the invention. One embodiment can be used to perform emergency cutting of a victim, removal of material, etching, marking and cauterizing of wounds. One embodiment allows the beam to cut through any obstacles. In one embodiment, the system can be used to gain access, open, cut into, or other wise free a person or object. One embodiment can be used to cut the top of a vehicle loose, I-beam, wood, metal, plastic, carbon fiber, cloth or fiberglass.

As illustrated in FIG. 1. in one embodiment, the man-portable system, e.g. system 100, is used in a hospital. One embodiment includes a handheld probe, a vest and movable cart and power supplied from a wall plug. Another embodiment includes wheels on the cart. Another embodiment includes a 120 volt or 240 Volt power supply. One embodiment, the handheld probe, e.g. handheld probe 115, includes a beam-scanners and optical delivery fibers. In one embodiment, the vest can include an optical compressors, e.g. compressor 110. In another embodiment, optical amplifiers e.g. amplifier 105, are positioned on or in the cart. In one embodiment, the cart includes a control module, e.g. control module 125; a control panel, e.g. control panel 130; a pulse generator, e.g. pulse generator 135; a power supply, e.g. power 120; a video camera, e.g. video camera 140; a video monitor, e.g. video monitor 145; an air flush system, e.g. air flush system 150, a suction system, e.g. suction system 155; and a marker beam generator, e.g. marker beam generator 160.

The concentration of pulse energy on a small spot enables the use of semiconductor-optical amplifiers or moderate-power fiber-amplifiers, as well as higher power Cr:YAG amplifiers. One embodiment includes a short initial optical pulse allows compression into a short pulse with an efficient and physically small compressor. Another embodiment has multiple semiconductor amplifiers or fiber amplifiers. In one embodiment, the amplifiers are Cr:YAG amplifiers. In one embodiment, the amplifier has a short (e.g., 1 nanosecond or less) initial optical pulse that undergoes controlled amplification and is then compressed into a short (sub-picosecond)

pulse, and the light pulse focused onto a small area, e.g., spot. In one embodiment, the area is between about 10 and about 50 microns in diameter. In one embodiment, the spot is scanned over an area to be ablated, wherein a controllable rate of ablation is achieved. One embodiment controls the amplifiers by controlling pulse power. One embodiment independently controls the ablation rate and pulse energy of multiple moderate-power amplifiers. In another embodiment, the amplifier is easily cooled. Thus, by the use of a combination of innovations, can now provide an efficient, reasonably priced, man-portable ablation system for medical and other purposes.

One embodiment includes a laser-amplifier and compressor that allow the system size is reduced, whereby the system to be man-portable. In one embodiment a semiconductor oscillator-driven pulse generator is used to generate a pulse between about ten picoseconds and about one nanosecond wavelength-swept-with-time. In one embodiment, the initial pulse is amplified by an optically-pumped amplifier. In one embodiment, the amplifier is an erbium-doped fiber amplifier or EDFA or a Cr:YAG amplifier. In one embodiment, the pulse is compressed by an air-path between gratings compressor or a Treacy grating air-grating compressor, wherein the compression creates a sub-picosecond ablation pulse. One embodiment has semiconductor optical amplifier (SOA) and a chirped fiber compressor, wherein the pulse is between about one to twenty nanosecond. In one embodiment, a semiconductor generates the initial pulse and a SOA preamplifier to amplify the initial pulse before introduction into the amplifier.

Different embodiments can be used for different applications depending on the specific needs of that application. One embodiment uses an optically-pumped—amplifier and air-grating-compressor to reduce cost, but another embodiment uses a SOA and chirped-fiber-compressor to produce an efficient and small system.

Ablative material removal can be done either in-vivo or on the body surface. As some materials ablate much faster than others and material is most efficiently removed at pulse energy densities about three times the materials ablation threshold. In one embodiment, the ablation rate is controlled. In one embodiment, the pulse energy densities is controlled to produce a pulse energy densities about three times the materials ablation threshold. In one embodiment, the surgical ablation has a threshold of less than one Joule per square centimeter, however other embodiments have an ablation threshold of up to about two Joules per square centimeter.

Again, as materials ablate at different thresholds, efficient operation requires control of the pulse energy density. One embodiment controls the pulse energy, thereby controlling the pulse energy density. One embodiment uses a fiber amplifier operating at high repetition rates. One embodiment controls the pulse energy by controlling the optical pumping power. Another embodiment controls the pulse energy by controlling the pulse repetition rate. In another embodiment, the system is fine tuned by controlling optical pumping power.

In one embodiment, the pulse energy is controlled by repetition rate and optically pumped amplifier operating temperature is controlled through controlling optical pumping power. In one embodiment, the pulse energy of semiconductor optical amplifiers (SOAs) is adjusted by changing the amplifier current. In one embodiment, the pulse energy applied to the body is between about 2.5 and about 3.6 times the ablation threshold of the body portion being ablated.

In one embodiment, the ablation rate is controlled independent of pulse energy. The use of two or more amplifiers in a train mode (pulses from one amplifier being delayed to arrive at the spot one or more nanoseconds after those from another amplifier) allows step-wise control of ablation rate independent of pulse energy density. Without this delay, the efficiency is significantly reduced. The use of train-mode amplifiers in either type of system provides faster ablation, while providing greater cooling surface area to minimize thermal problems. In one embodiment, two or more amplifiers are operated in a train mode. At lower desired ablation rates, one or more amplifiers can be shut down. In one embodiment, one or more amplifiers in train mode are shut down.

As illustrated in FIG. 2. one embodiment of the present invention includes a method of material removal using surgical ablative, either from an in-vivo surface or from an outside surface with a short optical pulse that is amplified and then compressed, comprising: Step 200, generating an initial wavelength-swept-with-time pulse in a pulse generator within a man-portable system; Step 210, amplifying the initial pulse and then Step 220, compressing the amplified pulse within the man-portable system, wherein the amplifying and compression are done with either an optically-pumped-amplifier and air-path between gratings compressor combination, or a SOA and chirped fiber compressor combination; and Step 230, applying the compressed optical pulse to the surface.

In one embodiment, the amplifying and compressing is done with an optically-pumped-amplifier and an air-path between gratings compressor combination, wherein the pulses are between about ten picoseconds and about one nanosecond. In another embodiment, the amplifying and compressing is done with a SOA/chirped-fiber-compressor combination, wherein the initial pulses between about one and about twenty nanoseconds.

Another embodiment includes a method of ablative material removal, from a surface or with a short optical pulse that is amplified and then compressed, comprising: generating an initial pulse in a pulse generator; amplifying the initial pulse and then compressing the amplified pulse within the man-portable system, wherein the amplifying is done with either an optically-pumped-amplifier or a SOA; compressing the amplified pulse to a duration of less than one picosecond; and applying the compressed optical pulse to the surface, wherein the generating, amplifying and compressing are done within a man-portable system. In one embodiment, two or more optically-pumped optical amplifiers or SOA optical amplifiers are used in a train mode and the compressed optical pulse is applied to the surface in a small area spot, wherein the spot area is between about ten and about 50 microns in diameter. In one embodiment, the pulse generator is semiconductor oscillator-driven.

In one embodiment, the amplifying and compressing is done with an optically-pumped-amplifier and air-path between gratings compressor combination, wherein the initial pulses are between about ten picoseconds and about one nanosecond. In one embodiment, the fiber amplifier is an erbium-doped or erbium/ytterbium fiber amplifier and the air-path between gratings compressor is a Treacy grating compressor. In one embodiment, two or more fiber amplifiers are used with one compressor. In another embodiment, the amplifier is an SOA and the compressor is a chirped optical fiber. In other embodiments, the pulse energy density and ablation rate are independently controlled. In other embodiments, the fiber amplifier and the amplifier temperature can be independently controlled.

High ablative pulse repetition rates are preferred and the total pulses per second (the total system repetition rate) from the one or more (train mode) optical amplifiers is preferably greater than 0.6 million. In one embodiment, the ablative pulse repetition rates are 0.6 million or more.

DETAILED DESCRIPTION OF THE INVENTION

Figure 1:
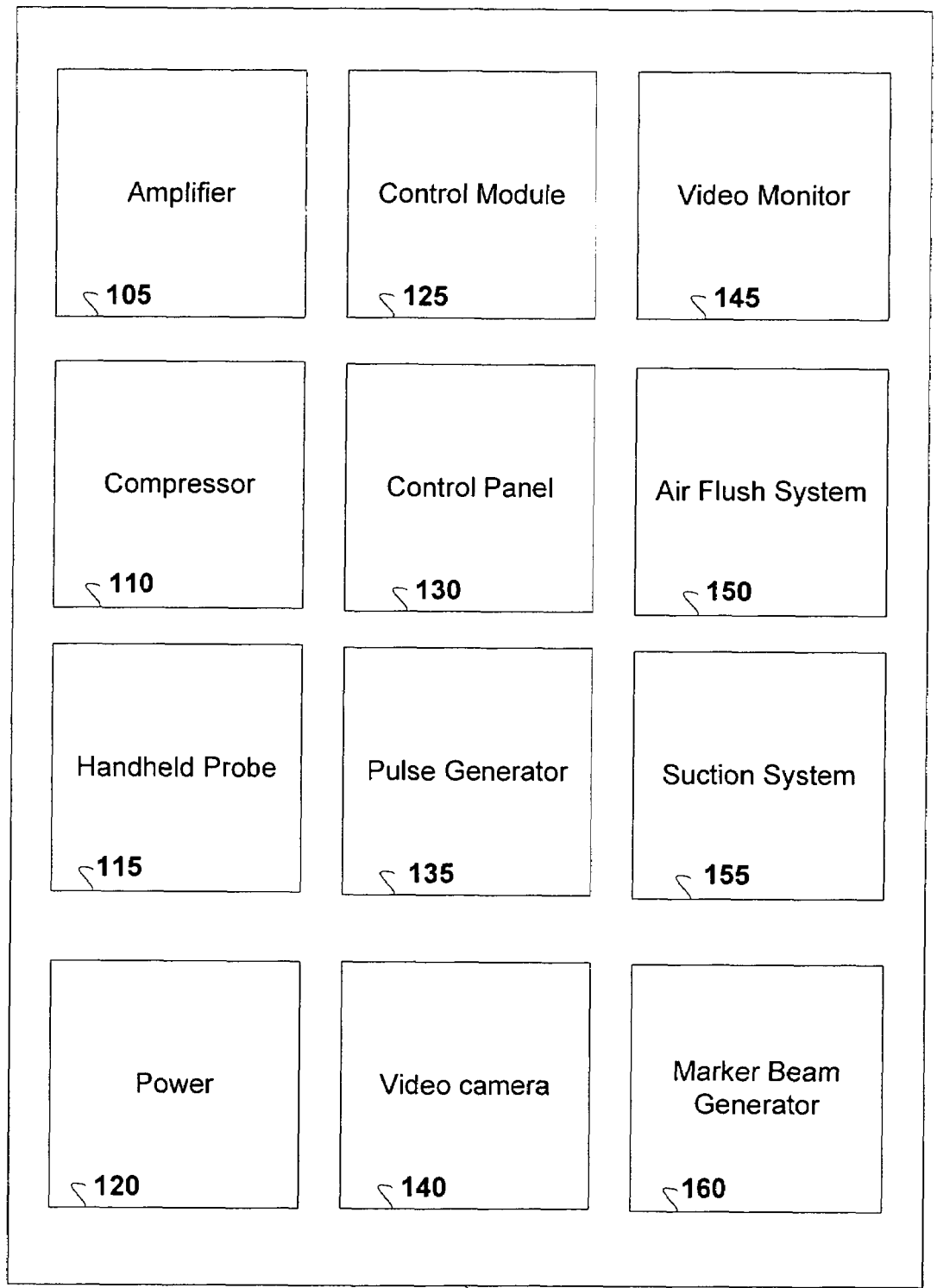
FIG. 1 is a block diagram of a system implementing one embodiment of the invention.
Figure 2:
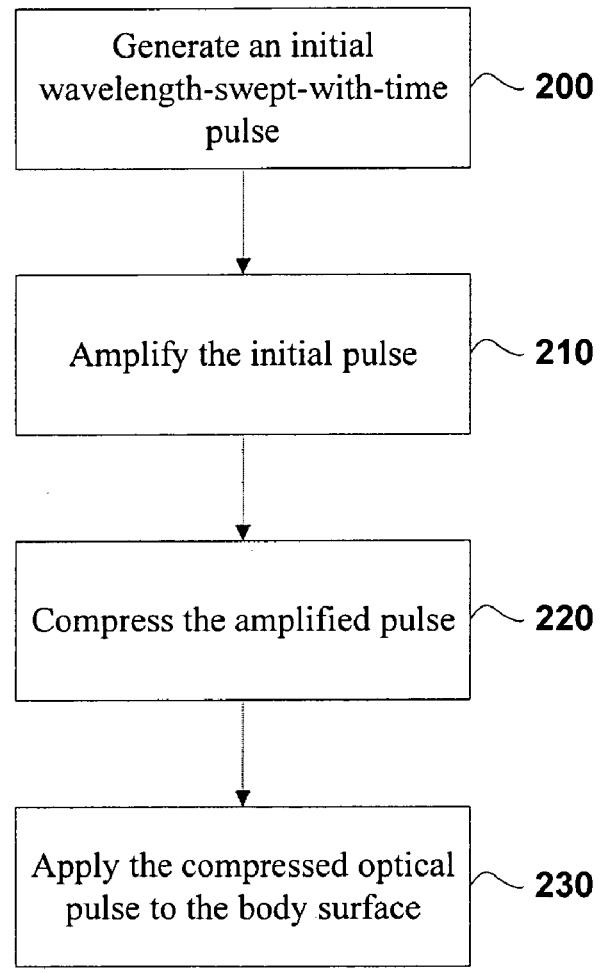
FIG. 2 is a flowchart illustrating the method used in one embodiment of the invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Ablative material removal previously this has been done using systems with optical benches weighing perhaps 1,000 pounds and occupying about 300 cubic feet. Previous approaches have generally operated maximum-sized amplifiers at maximum-power and amplifying longer-and-longer pulses.

In one embodiment, the man-portable unit is used in a hospital and includes a handheld probe, a vest, control-cart and receive power from a wall plug. In one embodiment, the handheld probe contains beam-scanners and optical delivery fibers. In one embodiment, the vest contains optical compressors and the optical amplifiers are positioned in the cart. In one embodiment, the cart contains the control module, the control panel, the pulse generator, the power supplies, a video camera, a video monitor, air flush system, a suction system and a marker beam generator.

In one embodiment, the optical-fiber-containing umbilical cables are used between components. In one embodiment, the umbilical includes a hollow ablation fiber for pulses compressed to sub-picosecond duration. One embodiment, the fiber is a hollow optical fibers, a video-camera fiber, an illumination fiber, a marker-beam fiber, an air flush tube, a suction tube and wiring for the scanners.

One embodiment is battery-powered and contains a probe, vest, backpack and one or more satchels. In one embodiment, the handheld probe contains beam-scanners and optical delivery fibers. One embodiment includes a vest containing optical compressors, optical amplifiers and control devices. In one embodiment, the control devices are control knobs, switches, buttons, dial or pad, positioned in or on the cart. In one embodiment, the backpack contains the control module, the pulse generator, the power supplies, a marker beam generator, and a battery pack. In one embodiment, the satchel contains a video camera, a video monitor, an illumination source, and additional batteries. One embodiment is operable without the satchel. Another embodiment includes the video camera in the backpack and a heads-up display providing a video monitor and a display of control settings.

In one embodiment, the handheld probe contains piezo-electrically-driven-mirror beam-scanners and optical delivery fibers. In one embodiment, the delivery fiber has a lens on the fiber-end near the probe tip and transmits a video image back to the video camera. In another embodiment, a fiber illuminates the ablation region. In another embodiment, a hollow optical fiber brings ablation pulses to the beam-scanner mirrors. In another embodiment, a fiber is used to bring a laser marker beam to the beam-scanner mirrors. In another embodiment, the marker beam is scanned. In one embodiment, the laser marker beam shows the entire scan area, however other embodiments turn the beam off and on by the specifications of area, color and distance from target. Another embodiment shows the area that would be ablated if the ablation beam were on. In other embodiments, the marker beam changes color to indicate whether the ablation beam is on or off. In another embodiment, the probe contains tubes for suction and/or gas flush.

One embodiment, the man-portable units includes a handheld probe, handheld probe, vest/backpack and one or more satchels. The unit can be relatively inexpensive and can be used by surgeons, doctors, dentists, scientists and emergency personnel in the field. However, those skilled in the art will recognize other uses for the invention. In one embodiment, the unit can be used to cut a victim and cauterize wounds. In another embodiment, the system uses microsecond long, thermally-inducing, pulses to cauterize a wound. One embodiment can be used to perform emergency cutting of a victim or an object, removal of material, etching, marking and cauterizing of wounds. One embodiment allows the beam to cut through any obstacles. In one embodiment, the system can be used to gain access, open, cut into, or otherwise free a person of object. One embodiment can be used to cut the top of a vehicle, I-beam, wood, metal, plastic, carbon fiber, cloth or fiberglass.

One embodiment uses one or more optically-pumped amplifiers of moderate-power, with a short optical pulse that is amplified and then compressed into a short pulse with the light pulse focused onto a small area spot. One embodiment of the present invention rapidly scans the spot over an area to be ablated and controls the pulse power to maximize ablation efficiency.

One embodiment controls the ablation rate and controls the pulse energy density in the ablation spot. If the spot size is fixed or otherwise known, this can be achieved by controlling pulse energy; or if the pulse energy is known, by controlling spot size. In one embodiment using optically-pumped amplifiers, the pulse energy is controlled step-wise by controlling repetition rate and fine-tuned by controlling optical pumping power. In another embodiment, the pulse energy of a semiconductor optical amplifier (SOA) is adjusted by changing the current thru the amplifier.

Further, it is preferred that ablation rate be controllable independent of pulse energy. One embodiment allows step wise control of the ablation rate independent of pulse energy through using two or more amplifiers in parallel a train mode (pulses from one amplifier being delayed to arrive one or more nanoseconds after those from another amplifier). Other embodiments allow a lower ablation rates by shutting off one or more amplifiers (e.g., the optical pumping to the fiber amplifier shut off), whereby there will be fewer pulses per train. One embodiment uses 20 amplifiers producing a maximum of 20 pulses in a train, however other embodiments use three or four amplifiers producing three or four pulses per train.

Generally, the optical amplifiers are pumped by laser diodes operating quasi-continually and are amplifying about 100,000 times per second for one nanosecond pulses. One embodiment uses optical amplifiers pumped by laser diodes. Another embodiment uses non-CW-pumping in operating amplifiers, whereby the amplifiers run in a staggered fashion, e.g., on for a first one second period and then turned off for one second period, and a first-period-dormant amplifier turned on during the second period, and so forth, to spread the heat load.

In some embodiments, the system is man-portable and includes a wheeled cart or a backpack. As used herein, the term "man-portable" means a system utilizing an optical amplifier that is either an optically-pumped-amplifier or a SOA with components that can be positioned by one man (e.g., as opposed to being mounted on a optical bench weighing hundreds of pounds), regardless of whether the system is designed to be easily moved or not. One embodiment includes an optically-pumped-amplifier with a compressor sized for a compression of between about ten picoseconds and about one nanosecond, or a SOA with a chirped-fiber-compressor, and which is designed to be reasonably easily moved.

One embodiment includes a method of ablative material removal, from a surface with a short optical pulse that is amplified and then compressed, including generating an initial pulse in a pulse generator within a man-portable system; amplifying the initial pulse and then compressing the amplified pulse within the man-portable system, wherein the amplifying and compression are done with either a fiber-amplifier and about ten picosecond and about one 1 nanosecond pulse-compressor combination, or a SOA and chirped fiber compressor combination; and applying the compressed optical pulse to the surface.

In one embodiment, the amplifying and compressing is accomplished with an optically-pumped-amplifier and air-path between gratings compressor combination. In one embodiment, the oscillator pulses is between about ten picoseconds and about one nanosecond. In another embodiment, the amplifying and compressing is done with a chirped fiber compressor combination. In one embodiment, the amplified pulses is between about one and about twenty nanoseconds in duration.

We have now found that certain laser-amplifier, compressor combinations enable practical, and significant size reduction, which in turn enables the system to be man-portable. One embodiment includes a man-portable system capable of being moved reasonably easily by one person. In one embodiment, the system includes a wheeled cart or possibly even being carried in a backpack, whereby the system is moveable from room to room. One embodiment uses initial pulses of between about ten picoseconds and about one nanosecond, with the initial pulse amplified by an optically-pumped-amplifier and compressed by an air-path between gratings compressor, with the compression creating a sub-picosecond ablation pulse. In one embodiment, the amplifier is an erbium-doped fiber amplifier or EDFA amplifier. In one embodiment, the grating compressor is a Treacy grating compressor.

Another embodiment uses a semiconductor optical amplifier (SOA) and a with a chirped fiber compressor. In one embodiment uses pulses of between about one and about twenty nanosecond during amplification. One embodiment uses a semiconductor generated initial pulse and a SOA preamplifier to amplify the initial pulse before introduction into the fiber amplifier.

While the compressors in either type of system can be run with inputs from more than one amplifier, reflections from other parallel (as used herein, "parallel" includes train mode) amplifiers can cause a loss of efficiency, and thus should be minimized. The loss is especially important if the amplifiers are amplifying signals at the same time, as is the case with the SOAs. In one embodiment each of the parallel SOAs has its own compressor, wherein the amplified pulses are then put into a single fiber after the compressors, whereby reflections from the joining (e.g., in a star connector) are reduced greatly before getting back to the amplifier. In one embodiment one or more fiber amplifiers are used with a single compressor, whereby the nanosecond spacing of sub-nanosecond pulses minimizes amplifying of multiple signals at the same time.

Fiber amplifiers have a storage lifetime of about 100 to 300 microseconds and for ablations purposes; fiber amplifiers have generally heretofore been operated with a time between pulses of almost equal to or greater than the storage lifetime, and thus are generally run a rep rate of less than 3-10 kHz. Fiber amplifiers are available with average power of 30 W or more. One embodiment uses a moderate-power 5 W average power fiber amplifiers producing pulses of about 500 microjoules or more to produce energy densities above the ablation threshold needed for non-thermal ablation, and increasing the energy in such a system, increases the ablation rate in either depth or allows larger areas of ablation or both.

In one embodiment an optically-pumped amplifier with a time between pulses of a fraction of the storage lifetime is used. In one embodiment, the optically-pumped amplifier with a time between pulses of about one-half or less of the storage lifetime. In one embodiment, a smaller spot is scanned to produce a larger effective ablation area. In one embodiment, the spot is about 50 microns or less in diameter. Other embodiments produce spots of about 60 or 75 microns or more. Spot sizes herein are given as circle diameter equivalents, a "50 micron" spot has the area of a 50 micron diameter circle, but the spot need not be round.

One embodiment uses parallel amplifiers to generate a train of pulses to increase the ablation rate by further increasing the effective repetition rate, whereby avoiding thermal problems. Another embodiment allows control of ablation rate by the use of a lesser number of operating fiber amplifiers. Another embodiment uses a SOA preamplifier to amplify the initial pulse before splitting to drive multiple parallel fiber amplifiers and another SOA before the introduction of the signal into each amplifier, whereby rapid shutting down of individual amplifiers can be achieved. Other embodiments operate with pulses at about three times the ablation threshold for greater ablation efficiency.

One embodiment uses about a 1 ns pulse with an optically-pumped amplifier and air optical-compressor to produce compression with approximately 40% losses. In one embodiment, the compressor is a Treacy grating compressor. At lower compressions, e.g., less than 1 nanosecond, the losses in a Treacy grating compressor are generally lower. If the other-than-compression losses are 10%, two nanoJoules are needed from the amplifier to get one nanoJoule on the target. One embodiment uses 1550 nm light. The use of greater than one nanosecond pulses in an air optical-compressor presents two problems; the difference in path length for the extremes of long and short wavelengths needs to be more three cm and, thus, the compressor is large and expensive, and the losses increase with a greater degree of compression.

Another embodiment uses a semiconductor optical amplifier (SOA) and a chirped fiber compressor is generally run with pulses of between about one and twenty nanosecond during amplification, and is operated at repetition rates with a time between pulses of more that the semiconductor storage lifetime. Another embodiment uses a SOA preamplifier to amplify the initial pulse before splitting to drive multiple SOAs. One embodiment scans a small ablation spot over a larger effective ablation area. In some embodiments with SOA Amplifiers a scanned spot that is smaller than the optically-pumped amplifier spot. One embodiment uses a semiconductor generated initial pulse.

Parallel amplifiers can be used to generate a train of pulses to increase the ablation rate by further increasing the effective repetition rate. Again, the pulse energy densities at operated at about three times the ablation threshold. One embodiment uses two or more amplifiers in parallel train mode, wherein pulses from one amplifier being delayed to arrive one or more nanoseconds after those from another amplifier. Other embodiments one or more amplifiers can be shut off producing fewer pulses per train. In one embodiment twenty amplifiers are used to produce a maximum of 20 pulses in a train, however, other embodiments use three or four amplifiers producing three or four pulses per train. In one embodiment, CW operation is used for operating amplifiers, wherein amplifiers might be run for e.g., one second and then turned off and a dormant amplifier turned on to spread the heat load.

In one embodiment controls the input optical signal power, optical pumping power of fiber amplifiers, timing of input pulses, length of input pulses, and timing between start of optical pumping and start of optical signals to control pulse power, and average degree of energy storage.

One embodiment includes an optical fibers have a maximum power of 4 MW, and thus, a 10-microJoule ablation pulse is amplified for a period as short as two picosecond. Thus, a fiber amplifier with this type of fiber can operates with an about ten ps, about 10 microJoule pulse, at 500 kHz (or 50 microJoule with 100 kHz). However, in embodiments where heating is a problem, multiple fiber amplifiers can be operated in a rotating mode. One embodiment rotates the operation of ten fiber amplifiers such that only five were operating at any one time (e.g., each on for $\frac{1}{10}^{th}$ of a second and off for $\frac{1}{10}^{th}$ of a second).

One embodiment includes ten optically-pumped amplifiers with time spaced inputs e.g., by 1 ns, to give a train of one to 10 pulses. One embodiment uses 5 W amplifiers operating at 100 kHz (and e.g., 50 microjoules) and step between 100 kHz and 1 MHz. With 50% post-amplifier optical efficiency and about 50 microjoules, to get about six J/sq. cm on the target, the spot size would be about 20 microns.

One embodiment includes 20 amplifiers with time spaced inputs, e.g., by 1 ns, to giving a train of one to 20 pulses, 5 W amplifiers operating at 50 kHz (and e.g., 100 microjoules) this can step between 50 kHz and 1 MHz. With 50% post-amplifier optical efficiency and 100 microjoules, to get 6 J/sq. cm on the target, the spot size would be about 33 microns. The amplified pulse is between about 50 and about 100 picoseconds long. One embodiment includes 10 amplifiers at 50 kHz to step between 50 kHz and 500 kHz.

Generally, it is the pulse generator that controls the input repetition rate of the amplifiers to tune energy per pulse. Another embodiment includes 5 W amplifiers operating at 20 kHz (and e.g., 250 microjoules). With 10 amplifiers this can step between 20 kHz and 200 kHz. With 50% post-amplifier optical efficiency and 250 microjoules, to get 6 J/sq. cm on the target, the spot size would be about 50 microns. The amplified pulse is between 100 to 250 picoseconds long. Another embodiment includes 30 amplifiers that steps between 20 kHz and 600 kHz.

Although very-high power SOA's can be built, they are quite expensive and generally require large cooling systems. Therefore one embodiment uses a SOA with a lower power and a longer period of amplification, from about one and about twenty nanoseconds, and preferably between about five and about twenty nanoseconds. Air-grating compressors are impractically large at these time periods. Therefore one embodiment of the man-portable SOA amplifier systems uses chirped fiber gratings (such gratings are commercially available from 3M). Another embodiment uses fiber amplifiers and use chirped fiber gratings, whereby these fiber gratings can be shorter, with less compression than those used with our SOAs.

Another embodiment generates a sub-picosecond pulse and time stretching that pulse within semiconductor pulse generator to give the initial wavelength-swept-with-time pulse.

One embodiment uses light leakage from the delivery fiber to get feedback proportional to pulse power and/or energy for control purposes. One embodiment measures the spot size with a video camera or a linear scan. One embodiment uses an "in-vivo" type camera (see "Camera Containing Medical Tool" U.S. Provisional Patent Applications, Ser. No. 60/472,071; filed May 20, 2003; which is incorporated by reference herein). One embodiment includes a handheld beam-emitting probe that provides its own illumination. Other embodiments include cameras using an optical fiber in a probe to convey an image back to a remote camera body. Another embodiment includes a vidicon-containing camera with a GRIN fiber lens. Still other embodiments use endoscope type cameras.

One embodiment scans a smaller ablation areas by moving the beam without moving the probe. Another embodiment scans a large areas by moving the beam over a first area, and then stepping the probe to second portion of the large area and then scanning the beam over the second area, and so on. One embodiment uses a beam deflecting mirrors mounted on piezoelectric actuators to move the beam (see "Scanned Small Spot Ablation With A High-Rep-Rate" U.S. Provisional Patent Applications, Ser. No. 60/471,972, filed May 20, 2003; which is incorporated by reference herein). One embodiment scans the actuators over a larger region but with the ablation beam only enabled to ablate portions with defined color and/or area. One embodiment allows evaluation after a prescribed time through preset combination of time and, area and/or color.

Information of such a system and other information on ablation systems are given in co-pending provisional applications listed in the following paragraphs (which are also at least partially co-owned by, or exclusively licensed to, the owners hereof) and are hereby incorporated by reference herein (provisional applications listed by docket No., title and United States Provisional Patent Applications, Serial Number):

Laser Machining—U.S. Provisional Patent Applications, Ser. No. 60/471,922; "Camera Containing Medical Tool" U.S. Provisional Patent Applications, Ser. No. 60/472,071; "Scanned Small Spot Ablation With A High-Rep-Rate" U.S. Provisional Patent Applications, Ser. No. 60/471,972; and "Stretched Optical Pulse Amplification and Compression", U.S. Provisional Patent Applications, Ser. No. 60/471,971, were filed May 20, 2003;

"Controlling Repetition Rate Of Fiber Amplifier" U.S. Provisional Patent Applications, Ser. No. 60/494,102; "Controlling Pulse Energy Of A Fiber Amplifier By Controlling Pump Diode Current" U.S. Provisional Patent Applications, Ser. No. 60/494,275; "Pulse Energy Adjustment For Changes In Ablation Spot Size" U.S. Provisional Patent Applications, Ser. No. 60/494,274; "Ablative Material Removal With A Preset Removal Rate or Volume or Depth" U.S. Provisional Patent Applications, Ser. No. 60/494,273; "Fiber Amplifier With A Time Between Pulses Of A Fraction Of The Storage Lifetime"; "Controlling Temperature Of A Fiber Amplifier By Controlling Pump Diode Current" U.S. Provisional Patent Applications, Ser. No. 60/494,322; "Altering The Emission Of An Ablation Beam for Safety or Control" U.S. Provisional Patent Applications, Ser. No. 60/494,267; "Enabling Or Blocking The Emission Of An Ablation Beam Based On Color Of Target Area" U.S. Provisional Patent Applications, Ser. No. 60/494,172; "Remotely-Controlled Ablation of Surfaces" U.S. Provisional Patent Applications, Ser. No. 60/494,276 and "Ablation Of A Custom Shaped Area" U.S. Provisional Patent Applications, Ser. No. 60/494,180; were filed Aug. 11, 2003. "High-Power-Optical-Amplifier Using A Number Of Spaced, Thin Slabs" U.S. Provisional Patent Applications, Ser. No. 60/497,404 was filed Aug. 22, 2003;

Co-owned "Spiral-Laser On-A-Disc", U.S. Provisional Patent Applications, Ser. No. 60/502,879; and partially co-owned "Laser Beam Propagation in Air", U.S. Provisional Patent Applications, Ser. No. 60/502,886 were filed on Sep. 12, 2003. "Active Optical Compressor" U.S. Provisional Patent Applications, Ser. No. 60/503,659, filed Sep. 17, 2003;

"High Power SuperMode Laser Amplifier" U.S. Provisional Patent Applications, Ser. No. 60/505,968 was filed Sep. 25, 2003, "Semiconductor Manufacturing Using Optical Ablation" U.S. Provisional Patent Applications, Ser. No. 60/508,136 was filed Oct. 2, 2003, "Composite Cutting With Optical Ablation Technique" U.S. Provisional Patent Applications, Ser. No. 60/510,855 was filed Oct. 14, 2003 and "Material Composition Analysis Using Optical Ablation", U.S. Provisional Patent Applications, Ser. No. 60/512,807 was filed Oct. 20, 2003;

"Quasi-Continuous Current in Optical Pulse Amplifier Systems" U.S. Provisional Patent Applications, Ser. No. 60/529,425 and "Optical Pulse Stretching and Compressing" U.S. Provisional Patent Applications, Ser. No. 60/529,443, were both filed Dec. 12, 2003;

"Start-up Timing for Optical Ablation System" U.S. Provisional Patent Applications, Ser. No. 60/539,026; "High-Frequency Ring Oscillator", U.S. Provisional Patent Applications, Ser. No. 60/539,024; and "Amplifying of High Energy Laser Pulses", U.S. Provisional Patent Applications, Ser. No. 60/539,025; were filed Jan. 23, 2004;

"Semiconductor-Type Processing for Solid-State Lasers", U.S. Provisional Patent Applications, Ser. No. 60/543,086, was filed Feb. 9, 2004; and "Pulse Streaming of Optically-Pumped Amplifiers", U.S. Provisional Patent Applications, Ser. No. 60/546,065, was filed Feb. 18, 2004. "Pumping of Optically-Pumped Amplifiers", was filed Feb. 26, 2004.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

What is claimed is:

1. A method of surgical ablative material removal from a body using a short optical pulse that is amplified and then compressed, comprising the steps of:
   generating an initial wavelength-swept-with-time pulse in a pulse generator;
   amplifying the initial wavelength-swept-with-time pulse using an optical amplifier, to generate an amplified pulse;
   compressing the amplified pulse within a man-portable system, to generate a compressed optical pulse, wherein the amplification and compression are performed using either an optically-pumped-amplifier and air-path between gratings compressor combination, or a semiconductor optical amplifier and chirped fiber compressor combination; and
   applying the compressed optical pulse to the body, wherein the pulse generation, amplification and compression are performed within the man-portable system.

2. The method of claim 1, wherein more than one optical amplifiers are operated in a train mode to amplify the wavelength-swept-with-time pulse.

3. The method of claim 1, wherein the compressed optical pulse is applied to a surface of the body as a circular spot having a diameter between about 10 and about 50 microns.

4. The method of claim 1 wherein the man-portable system comprises a wheeled cart.

5. The method of claim 1 wherein the pulse generator is semiconductor-oscillator driven.

6. The method of claim 1, wherein the amplifying and compressing steps are performed using a fiber-amplifier and air-path between gratings compressor combination, and
   the initial wavelength-swept-with-time pulse has a duration of between about ten picoseconds and about one nanosecond.

7. The method of claim 6, wherein the fiber-amplifier is an erbium-doped fiber-amplifier.

8. The method of claim 6, wherein the air-path between gratings compressor comprises a Treacy grating compressor.

9. The method of claim 6, wherein more than one fiber-amplifiers are operated in a train mode, and pulses from the more than one fiber-amplifiers are compressed using the air-path between gratings compressor.

10. A method of ablative material removal from a surface of a body, comprising the steps of:
    generating an initial pulse in a pulse generator;
    amplifying the initial pulse using an amplifier comprising either an optically-pumped-amplifier or a semiconductor optical amplifier within a man-portable system, to generate an amplified pulse;
    compressing the amplified pulse within the man-portable system using a compressor, to generate a compressed optical pulse having a duration of one picosecond or less; and
    applying the compressed optical pulse to the surface of the body, wherein the generating, amplifying and compressing steps are performed within the man-portable system.

11. The method of claim 10, wherein the amplifying and compressing steps are performed using a fiber-amplifier and an air-path between gratings compressor combination.

12. The method of claim 11, wherein the fiber-amplifier comprises an erbium-doped fiber amplifier.

13. The method of claim 11, wherein the air-path between gratings compressor comprises a Treacy grating compressor.

14. The method of claim 10, wherein the compressing step is performed using a chirped fiber compressor.

15. The method of claim 10, wherein the man-portable system comprises a wheeled cart.

16. The method of claim 10, wherein the man-portable system comprises a backpack.

17. The method of claim 10, wherein more than one amplifiers are used in a train mode to amplify the initial pulse.

18. The method of claim 17, wherein amplified pulses from more than one fiber-amplifiers are compressed using the compressor.

19. The method of claim 10, wherein pulse energy density and ablation rate are independently controlled.

20. The method of claim 10, wherein pulse energy density, fiber-amplifier operating temperature, and ablation rate are independently controlled.

21. A system for surgical ablative material removal from a body using a short optical pulse that is amplified and then compressed, comprising:

means for generating an initial wavelength-swept-with-time pulse in a pulse generator;

means for amplifying the initial wavelength-swept-with-time pulse using an optical amplifier, to generate an amplified pulse;

means for compressing the amplified pulse within a man-portable system to generate a compressed optical pulse, wherein the amplification and compression are performed using either an optically-pumped-amplifier and air-path between gratings compressor combination, or a semiconductor optical amplifier and chirped fiber compressor combination; and means for applying the compressed optical pulse to the body, wherein the pulse generation, amplification and compression are performed within the man-portable system.

22. The system of claim 21, wherein the means, for amplifying the initial wavelength-swept-with-time pulse includes more than one optical amplifier configured to be operated in a train mode to amplify the wavelength-swept-with-time pulse.

23. The system of claim 21, wherein the means for compressing the amplified pulse are configured to compress pulses from more than one fiber-amplifier.

24. system of claim 21, wherein the means for amplifying the initial wavelength-swept-with-time pulse is configured to independently control pulse energy density and ablation rate.

* * * * *